United States Patent [19]
Yoshida et al.

[11] 4,181,731
[45] Jan. 1, 1980

[54] NOVEL THERAPEUTIC APPLICATION OF 4-CARBAMOYL-5-HYDROXYIMIDAZOLE

[75] Inventors: Noboru Yoshida, Osaka; Takao Kiyohara, Ibaraki; Shigeo Ogino, Nishinomiya, all of Japan

[73] Assignee: Sumitomo Chemical Company, Limited, Osaka, Japan

[21] Appl. No.: 918,074

[22] Filed: Jun. 22, 1978

Related U.S. Application Data

[62] Division of Ser. No. 831,115, Sep. 7, 1977, abandoned.

[51] Int. Cl.$^2$ ............................................. A61K 31/415
[52] U.S. Cl. ................................................ 424/273 R
[58] Field of Search ......................................... 424/273

[56] References Cited
PUBLICATIONS

Proceeding of the First Inter Sectional Congress of Iams, 3, pp. 441–443 (1974).

Sakagudhi et al., J. Antibiotics, 28, pp. 798–803 (1975).

*Primary Examiner*—Jerome D. Goldberg
*Attorney, Agent, or Firm*—Birch, Stewart, Kolasch and Birch

[57] ABSTRACT

4-Carbamoyl-5-hydroxyimidazole representable by the following formula:

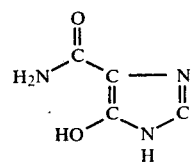

and pharmaceutically acceptable salts thereof have been found to be useful as therapeutic agents for the treatment of rheumatism and nephritis.

9 Claims, No Drawings

NOVEL THERAPEUTIC APPLICATION OF 4-CARBAMOYL-5-HYDROXYIMIDAZOLE

This application is a divisional of copending application Ser. No. 831,115, filed on Sept. 7, 1977, now abandoned.

The present invention relates to a novel therapeutic application of 4-carbamoyl-5-hydroxyimidazole, which is hereinafter referred to as Compound A, and its pharmaceutically acceptable salts.

Compound A has been known and disclosed in The Journal of the American Chemical Society, Vol. 74, p. 2892, (1952). However, its antirheumatic and antinephritic properties have never been studied prior to the present invention.

As the result of an extensive study on the pharmaceutical properties of Compound A, it has been found that Compound A has excellent antirheumatic as well as antinephritic activities and is useful as a therapeutic agent in the treatment of rheumatism and nephritis.

In the following, the antirheumatic and antinephritis activities and the toxicity of Compound A are described.

(1) Antirheumatic Activities

The antirheumatic activities on adjuvant arthritis were estimated according to the methods described in "Arzneimittel-Forschung (Drug Res.)", Vol. 22, p. 1959 (1972). The results are described in Table I.

Table I

Inhibitory effects on the adjuvant arthritis of rats.

| Dosage | Route | Foot Volume (ml) | Inhibition Rate (%) |
|---|---|---|---|
| Control | | 2.34 | — |
| 5 mg/kg/day × 21* | p.o. | 1.28 | 45.3 |
| 10 mg/kg/day × 21* | p.o. | 0.88 | 62.3 |
| 25 mg/kg/day × 21* | p.o. | 0.44 | 81.2 |

Note:
*Successive administration was performed immediately after inoculation of the adjuvant.

(2) Antinephritic Activities

The antinephritic activities were estimated according to the methods described in "Arerugii", Vol. 24, p. 472 (1975) (in Japanese). The results are described in Table II.

Table II

Antinephritic effects on *Masuji nephritis*.

| Dosage | Route | Urinary Protein (mg/24 hrs.) | Inhibition Ratio (%) |
|---|---|---|---|
| Control | | 238.9 | — |
| 5 mg/kg/day × 16* | p.o. | 147.6 | 38.2 |
| 10 mg/kg/day × 16* | p.o. | 68.4 | 71.4 |
| 25 mg/kg/day × 16* | p.o. | 28.4 | 88.1 |

Note:
*Successive oral administration began for 2 days before the injection of nephrotoxin.

(3) Acute toxicity

Acute toxicity of Compound A against mice (ICR, male, body weight 22–25 g) was as follows.

| Route | $LD_{50}$ |
|---|---|
| p.o. | greater than 2000 mg/kg |
| i.p. | greater than 500 mg/kg |
| i.v. | greater than 130 mg/kg |

(4) Subacute Toxicities

Subacute toxicities of Compound A against mice (ICR, male, body weight approximately 25 g) were as follows. The said compound was orally administered for 21 days. The dosage level was 100 mg/kg/day.

(i)

| Body weight change | Normal |
|---|---|
| Food consumption | Normal |

(ii) Haematology

| White blood cells | (average) $6.5 \times 10^4/mm^3$ |
|---|---|
| Red blood cells | (average) $6.0 \times 10^6/mm^3$ |
| Hemoglobin | (average) 15.1 g/dl |
| Hematocrit value | (average) 35% |
| GOT | (average) 54.4 K.U. |
| No adverse effect. | |

(ii) Urinalysis

| Protein | 30–100 mg/dl |
|---|---|
| Glucose | Negative |
| Occult blood | Negative |
| pH | 6.0–6.5 |
| No adverse effect. | |

(iv) Autopsy
No adverse effect.

(v) Relative organ weight (%)

| Liver | (average) 6.24 |
|---|---|
| Kidney | (average) 1.50 |
| Spleen | (average) 0.30 |
| Thymus | (average) 0.20 |
| Heart | (average) 0.49 |
| Testis | (average) 0.38 |
| Lung | (average) 0.81 |

(vi) Clinical signs
No adverse effect except slight involution of the spleen.

As stated above, it is evident that Compound A is an excellent therapeutic agent for rheumatism and nephritis with low toxicity. Moreover, it is an advantageous merit that the agent can be administered orally as well as by injection.

Compound A is active at dosage levels of 0.3–1.0 g per day for the adult when used in therapy of rheumatism or nephritis.

Compound A may be used in the free form, or preferably, in the form of a pharmaceutically acceptable addition salt thereof. Among these salts are, for example, the hydrochloride, the sodium salt, etc.

One of the preferred routes of administration is orally, in the form of an oral dosage unit, for example a tablet or capsule. A sustained capsule is also acceptable. These compositions are formulated in a manner well-known to pharmaceutical chemists, utilizing standard pharmaceutical excipients such as syrup, gum arabic, gelatin, sorbitol, tragacanth, polyvinylpyrrolidone, lactose, glucose, corn starch, calcium phosphate, glycine, magnesium stearate, talc, polyethylene glycol, silica, potato starch, sodium lauryl sulfate and so on. Tablets can contain correctives, dyestuffs, lubricants and so on.

Oral administration may also be effected using a liquid formulation, for example, a water or oil emulsion, solution, syrup, elixir, and other forms. Dried matter which is dissolved in water or other vehicles before use is also acceptable. These liquid preparations can contain the acceptable additives, for example, sorbitol syrup, methylcellulose, glucose/sugar syrup, hydroxyethylcellulose, carboxymethylcellulose, aluminum stearate gel, oil, wax lecithin, monooleic sorbitan, gum arabic, almond oil, fractionated coconut butter, oil esters, propylene glycol, ethyl alcohol, methyl p-hydroxybenzoate, propyl p-hydroxybenzoate, sorbic acid, and if necessary, dyestuffs, perfumes and so on.

Injectable compositions can contain aseptics and solubilizers. The compositions are also acceptable in the form of a suspension, solution or emulsion, and can contain suspenders, stabilizers, dispersers and so on. On the other hand, the active component may be presented in the powdery form which is dissolved in an appropriate vehicle such as pyrogen-free sterilized water before use.

These compositions can contain, at least, more than 0.1% by weight, preferably 10–60% by weight of the active compound. In the case that the composition is composed of the unit dosage form, it should preferably contain 5–250 mg of the active component.

When Compound A is administered intravenously, it should preferably be formulated into soluble forms such as the sodium salt or the hydrochloride.

Representative compositions containing the active component follow in the examples.

Example 1 (Injectable composition)

Sterile 4-carbamoyl-5-hydroxyimidazole hydrochloride (10 mg) was aseptically put into an ampoule and sealed to prevent humidity and microbial contamination. Before use, it was dissolved in 2 ml of 0.5% (w/v) lidocaine solution.

Example 2 (Injectable composition)

Manufacturing procedures were identical with Example 1 except the content of the active component (250 mg).

Example 3 (Injectable composition)

Sterile sodium 4-carboamoyl-5-hydroxyimidazolate (250 mg) was aseptically put into an ampoule and sealed to prevent humidity and microbial contamination. Before use, it was dissolved in 2 ml of 0.5% (w/v) lidocaine solution.

Example 4 (Injectable composition)

Manufacturing procedures were identical with Example 3 except the content of the active component (10 mg).

Example 5 (Tablet)

| | |
|---|---|
| 4-Carbamoyl-5-hydroxyimidazole | 250 mg |
| Mannitol | 200 mg |
| Potato starch | 47 mg |
| Magnesium stearate | 3 mg |

Example 6 (Suppositoria)

| | |
|---|---|
| 4-carbamoyl-5-hydroxyimidazole | 250 mg |
| Tannic acid | 15 mg |
| Belladonna extract | 10 mg |
| Ichthammol | 100 mg |
| Ethylaminobenzoate | 50 mg |
| Cacaobutter | 750 mg |

Example 7 (Suppositoria)

| | |
|---|---|
| 4-Carbamoyl-5-hydroxyimidazole | 500 mg |
| Tannic acid | 30 mg |
| Belladonna extract | 20 mg |
| Ichthammol | 200 mg |
| Ethylaminobenzoate | 100 mg |
| Cacaobutter | 1500 mg |

In addition, the said active component can be formulated into unguent, troche and like forms in a manner well-known to pharmaceutical chemists.

What is claimed is:

1. A method for the treatment of rheumatism and nephritis which comprises administering a composition containing an effective anti-rheumatic or anti-nephritic amount of 4-carbamoyl-5-hydroxyimidazole or a pharmaceutically acceptable salt thereof as an active ingredient and a pharmaceutically acceptable carrier or diluent to a patient suffering from rheumatism or nephritis.

2. A method for the treatment of rheumatism which comprises administering to a patient suffering from rheumatism a composition comprising an effective anti-rheumatic amount of 4-carbamoyl-5-hydroxyimidazole or a pharmaceutically acceptable salt thereof as an active ingredient and a pharmaceutically acceptable carrier or diluent.

3. A method according to claim 2, wherein said pharmaceutically acceptable salt of 4-carbamoyl-5-hydroxyimidazole is the hydrochloride or sodium salt thereof.

4. A method according to claim 2, wherein said composition is in the form of an injectable composition, tablet, capsule or suppository.

5. A method according to claim 2, wherein the daily dosage of the active ingredient is from 0.3 to 10 grams for an adult person.

6. A method for the treatment of nephritis which comprises administering to a patient suffering from nephritis a composition comprising an effective anti-nephritic amount of 4-carbamoyl-5-hydroxyimidazole or a pharmaceutically acceptable salt thereof as an active ingredient and a pharmaceutically acceptable carrier or diluent.

7. A method according to claim 6, wherein said pharmaceutically acceptable salt of 4-carbamoyl-5-hydroxyimidazole is the hydrochloride or sodium salt thereof.

8. A method according to claim 6, wherein said composition is in the form of an injectable composition, tablet, capsule or suppository.

9. A method according to claim 6, wherein the daily dosage of the active ingredient is from 0.3 to 10 grams for an adult person.

* * * * *

UNITED STATES PATENT AND TRADEMARK OFFICE
CERTIFICATE OF CORRECTION

PATENT NO. : 4,181,731
DATED : January 1, 1980
INVENTOR(S) : Noboru Yoshida et al.

It is certified that error appears in the above—identified patent and that said Letters Patent is hereby corrected as shown below:

On the title page insert Foreign Priority Data:

--- Sept. 7, 1976 (JP)    Japan    51-107520 ---.

Signed and Sealed this

Twenty-fourth Day of June 1980

[SEAL]

Attest:

SIDNEY A. DIAMOND

Attesting Officer

Commissioner of Patents and Trademarks